United States Patent [19]

Bissett

[11] Patent Number: 5,652,228
[45] Date of Patent: Jul. 29, 1997

[54] TOPICAL DESQUAMATION COMPOSITIONS

[75] Inventor: Donald L. Bissett, Hamilton, Ohio

[73] Assignee: The Procter & Gamble Company, Cincinnati, Ohio

[21] Appl. No.: 558,944

[22] Filed: Nov. 13, 1995

Related U.S. Application Data

[63] Continuation of Ser. No. 209,041, Mar. 9, 1994, abandoned, which is a continuation-in-part of Ser. No. 150,942, Nov. 12, 1993, abandoned.

[51] Int. Cl.$^6$ .................................................. A61K 31/685
[52] U.S. Cl. ........................ 514/77; 514/159; 514/556; 514/613; 514/642; 514/859
[58] Field of Search ............................. 514/77, 159, 613, 514/642, 859, 556

[56] References Cited

U.S. PATENT DOCUMENTS

| | | | |
|---|---|---|---|
| 4,107,328 | 8/1978 | Michaels | 424/316 |
| 4,287,174 | 9/1981 | Laughlin | 424/78 |
| 4,318,907 | 3/1982 | Kligman et al. | 424/230 |
| 4,800,197 | 1/1989 | Kowcz et al. | 514/162 |
| 5,091,171 | 2/1992 | Yu et al. | 424/642 |
| 5,100,656 | 3/1992 | Lang et al. | 424/70 |

FOREIGN PATENT DOCUMENTS

| | | | |
|---|---|---|---|
| 0273202 | 7/1988 | European Pat. Off. | A61K 47/00 |
| 56-065810 | 6/1981 | Japan | A61K 7/06 |
| 59-5107 | 1/1984 | Japan . | |
| 3-044314 | 2/1991 | Japan | A61K 7/13 |
| 64162 | 3/1978 | Romania . | |
| 1518683 | 7/1978 | United Kingdom | A61K 45/08 |
| WO91/17237 | 11/1991 | WIPO | C11D 17/00 |
| WOA9409755 | 5/1994 | WIPO | A61K 7/48 |

OTHER PUBLICATIONS

Reynolds, J.E.F. (Editor) Dermatological Agents, *The Pharmaceutical Press*, K. Parfitt, pp. 931–932 (1989).

Marcoin, W. "Studies of the Effect of Selected Amphotensides and Ointment Bases on the Pharmaceutical Availability of Therapeutic Substances in the Ointment", *Acta Polon. Pharm.*, XLVI No. 5–6, pp. 448–453, (1989).

Rom. 64,162: Chemical Abstracts, vol. 92, p. 328, (1980). Abstract Only.

*Primary Examiner*—Kevin E. Weddington
*Attorney, Agent, or Firm*—Loretta J. Henderson; John M. Howell; David L. Suter

[57] ABSTRACT

The subject invention relates to desquamation compositions comprising a combination of salicylic acid and certain zwitterionic surfactants. The subject invention further relates to methods of desquamation in mammalian skin and treating acne in mammalian skin.

30 Claims, No Drawings

TOPICAL DESQUAMATION COMPOSITIONS

This is a continuation of application Ser. No. 08/209,041, filed on Mar. 9, 1994, now abandoned which is a continuation-in-part of application Ser. No. 08/150,942, filed on Nov. 12, 1993 now abandoned.

TECHNICAL FIELD

The subject invention relates to the field of skin conditioning. Specifically, the subject invention relates to methods for improving the suppleness or smoothness of skin by removing scales from skin surface.

BACKGROUND

Skin is composed of two layers: the epidermis (or cuticle) and the dermis. The epidermis is a thin outer layer composed of stratified epithelium. The outermost layer of the epidermis is the stratum corneum which is composed of keratin protein-filled, flattened cells surrounded by thin lipid layers. The cells are believed to be attached to one another by protein connections (desmosomes) between cells. The cells in the deepest portion of the epidermis, the basal layer, multiply and grow, pushing the older cells of the epidermis upward and toward the surface. As these cells move upward they become flattened. The epidermis is generally devoid of blood vessels and depends on blood vessels found in the dermis for nutrition. The more superficial cells of the epidermis, being far removed from the nutrient supply, gradually differentiate, transforming their proteins into keratin. This process of keratinization results in the death of the cells. Keratin is an insoluble proteinaceous material and gives the stratum corneum a horn-like consistency. The outermost dead stratum corneum cells are gradually shed and replaced by more recently keratinized cells.

In normal skin, the stratum corneum is shed as individual cells or as small clusters of cells. Skin problems such as dry skin, psoriasis, ichthyosis, dandruff, acne, callus, photodamaged skin, aged skin, and sunburn can be described as disorders of keratinization in which the shedding of stratum corneum cells at the skin surface is altered relative to normal, young, healthy skin. Such alteration results in large clusters of cells leading to visible scaling of the skin, a build-up of keratinaceous material on the surface or in follicles or ducts and/or a rough texture to the skin surface. These conditions may be improved by removal of the outermost keratinaceous material.

For the foregoing reasons, there is a need for an efficacious agent for removing surface scales from the stratum corneum of mammalian skin.

It is an object of the subject invention to provide topical compositions for desquamation (scale removal) from the stratum corneum of mammalian skin.

It is a further object of the subject invention to provide such compositions which are gentler and less irritating to the skin than existing compositions.

It is also an object of the subject invention to provide methods for removal of scales in mammalian skin.

SUMMARY

The subject invention involves a combination of salicylic acid and certain zwitterionic surfactants having the structure:

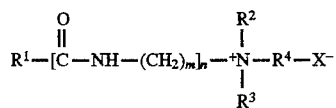

wherein
(a) $R^1$ is unsubstituted, saturated or unsaturated, straight or branched chain alkyl having from about 9 to about 22 carbon atoms;
(b) m is an integer from 1 to 3;
(c) n is 0 or 1;
(d) $R^2$ and $R^3$ are, independently, alkyl having from 1 to about 3 carbon atoms, unsubstituted or mono-substituted with hydroxy;
(e) $R^4$ is saturated or unsaturated, straight or branched chain alkyl, which is unsubstituted or mono-substituted with hydroxy, having from 1 to about 5 carbon atoms; and
(f) X is $CO_2$, $SO_3$ or $SO_4$.

Such a combination and compositions comprising it satisfy the need for an efficacious, easily administered agent for desquamation of skin, having little or no undesirable side effects. The subject invention is also directed to a method of removing scales in a mammal susceptible to or suffering from abnormal keratinization, comprising application of a composition of the subject invention. The subject invention is further directed to a method of treating acne in a mammal susceptible to or suffering from acne.

The compositions of the subject invention comprise a safe and effective amount of salicylic acid in combination with a safe and effective amount of certain zwitterionic surfactants, and a pharmaceutically-acceptable carrier.

These and other features, aspects and advantages of the subject invention will become better understood with reference to the following description and appended claims.

DETAILED DESCRIPTION OF THE INVENTION

It has been unexpectedly found that a combination of salicylic acid and certain zwitterionic surfactants exhibits the ability to remove scales from the stratum corneum in mammalian skin and scalp, without undesirable side effects. While the subject invention is not limited to any particular mode of action, it is believed that the subject combination works by affecting the skin surface's proteolytic enzyme which degrades the protein connections (desmosomes) between cells, thus causing cell or scale shedding. The subject invention thus activates the skin's natural desquamation process at the surface of problem skin.

As used herein "desquamation" means the shedding or removal of scales from the outermost layer (stratum corneum) of the epidermis.

As used herein "treating acne" means preventing, retarding and/or arresting the process of acne formation in mammalian skin.

As used herein, the term "alkyl", unless otherwise indicated, means carbon-containing chains which may be straight or branched, substituted or unsubstituted, saturated or unsaturated. Preferred alkyl are saturated. Preferred alkyl are straight chain. Preferred alkyl are unsubstituted.

As used herein "zwitterionic surfactant" means a compound having the structure:

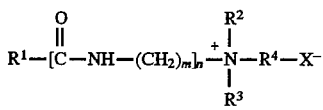

In structure (I) $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 16 carbon atoms; more preferably still from about 14 to about 16 carbon atoms.

In structure (I), m is an integer from 1 to 3, preferably 2 or 3; more preferably 3.

In structure (I), n is either 0 or 1; n is preferably 1.

In structure (I), $R^2$ and $R^3$ are, independently, selected from the group consisting of alkyl having from 1 to about 3 carbon atoms, unsubstituted or mono-substituted with hydroxy. Preferred $R^2$ and $R^3$ are $CH_3$.

In structure (I), X is selected from the group consisting of $CO_2$, $SO_3$ and $SO_4$.

In structure (I), $R^4$ is selected from the group consisting of saturated or unsaturated, straight or branched chain alkyl, unsubstituted or mono-substituted with hydroxy, having from 1 to about 5 carbon atoms. When $X=CO_2$, $R^4$ preferably has 1 or 3 carbon atoms, more preferably 1 carbon atom. When $X=SO_3$ or $SO_4$, $R^4$ preferably has from about 2 to about 4 carbon atoms, more preferably 3 carbon atoms.

Preferred zwitterionic surfactants of the subject invention include the following compounds:

a) cetyl betaine:

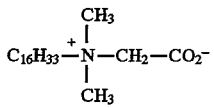

b) cocoamidopropylbetaine:

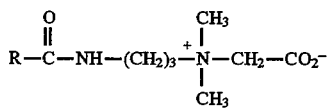

c) cetyl propyl hydroxy sultaine:

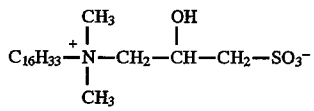

d) cocoamidopropyl hydroxy sultaine:

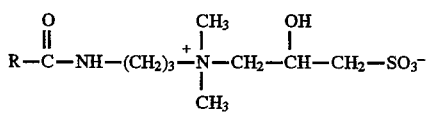

wherein R has from about 9 to about 13 carbon atoms; and e) behenyl betaine:

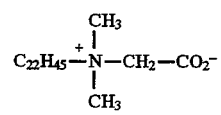

More preferred zwitterionic surfactants of the subject invention include cetyl betaine, cocoamidopropyl betaine and cetyl propyl hydroxy sultaine. Still more preferred zwitterionic surfactants of the subject invention include cetyl betaine and cocoamidopropyl betaine. The most preferred zwitterionic surfactant of the subject invention is cetyl betaine.

As used herein "topical application" means directly laying on or spreading on outer skin.

As used herein, "safe and effective amount" means a sufficient amount of a composition to significantly induce a positive modification in the condition being treated, but low enough to avoid serious side effects.

As used herein "comprising" means that other steps and ingredients which do not affect the end result can be added. This term encompasses the terms "consisting of" and "consisting essentially of".

As used herein, "pharmaceutically-acceptable" means that drugs, medicaments or inert ingredients which the term describes are suitable for use in contact with the tissues of humans and lower animals without undue toxicity, incompatibility, instability, irritation, allergic response and the like.

As used herein, "actives" or "active agents" means a combination of salicyclic acid, and a zwitterionic surfactant according to structure (I) or a mixture of such surfactants.

Compositions useful for desquamation preferably comprise from about 0.1% to about 10%, more preferably from about 0.2% to about 5%, also preferably about 0.5% to about 2% of salicylic acid or a pharmaceutically-acceptable salt thereof. Preferred pharmaceutically-acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium.

Compositions useful for desquamation also preferably comprise from about 0.1% to about 10%, more preferably from about 0.2% to about 5%, also preferably from about 0.5% to about 2% of zwitterionic surfactant according to structure (I) or a pharmaceutically-acceptable salt thereof. Preferred pharmaceutically-acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium.

Pharmaceutically-Acceptable Carrier

In addition to the active agents as described hereinbefore, the pharmaceutical compositions of the present invention essentially comprise a pharmaceutically-acceptable carrier. The term "pharmaceutically-acceptable carrier", as used herein, means one or more compatible solid or liquid filler diluents which are suitable for administration to a human or lower animal. The term "compatible", as used herein, means that the components of the pharmaceutical compositions are capable of being comingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

The compositions of the subject invention are administered topically to a biological subject, i.e., by the direct laying on or spreading of the composition on the skin of the subject. The topical compositions useful in the subject invention involve compositions suitable for topical application to mammalian skin, the composition comprising a safe and effective amount of the active agents or mixture of such actives as described hereinafter, and a pharmaceutically-acceptable topical carrier.

The topical compositions useful in the subject invention may be made into a wide variety of product types. These include, but are not limited to, lotions, creams, gels, sticks, sprays, ointments, pastes, mousses and cosmetics. These product types may comprise several types of carrier systems including, but not limited to solutions, emulsions, gels, solids, and liposomes.

The topical compositions useful in the subject invention formulated as solutions typically include a pharmaceutically-acceptable aqueous or organic solvent. The terms "pharmaceutically-acceptable organic solvent" refer to a solvent which is capable of having the actives dispersed or dissolved therein, and of possessing acceptable safety properties (e.g., irritation and sensitization characteristics). Water is a preferred solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, sorbitol esters, butanediol, and mixtures thereof. These solutions useful in the subject invention preferably contain from about 80% to about 99.99% of an acceptable aqueous or organic solvent.

If the topical compositions useful in the subject invention are formulated as an aerosol and applied to the skin as a spray-on, a propellant is added to a solution composition. Examples include chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972)

Topical compositions useful in the subject invention may be formulated as a solution comprising an emollient. Such compositions preferably contain from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from about 2% to about 10% of an emollient; and from about 0.1% to about 2% of a thickening agent. A more complete disclosure of thickening agents useful herein can be found in Sagarin, *Cosmetics, Science and Technology*, 2nd Edition, Vol. 1, pp. 72–73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317–324 (1986).

Preferred emulsions of the subject compositions have low levels of high molecular weight silicones (viscosities of about 50 centistokes or more). More preferred emulsions have viscosities of about 10 centistokes or less. Even more preferred emulsions have viscosities of about 5 centistokes or less. Also preferred emulsions are substantially free of high molecular weight silicones. Anti-foaming compositions are also preferably added because the absence of silicones, in some compositions, may cause foaming upon application. Preferred emulsions of the subject formula are substantially free of occlusives, such as petrolatum, which appear to diminish the zwitterionic effect. Preferred emulsions of the subject compositions are formulated at low pH values, preferably from about 2 to about 4, more preferably about 3. Preferred emulsions of the subject compositions contain humectants, such as glycerin.

The cleaning compositions useful in the subject invention preferably contain from about 1% to about 90%, more preferably from about 5% to about 10%, of a cosmetically-acceptable surfactant.

The physical form of the cleansing compositions is not critical. The compositions can be, for example, formulated as toilet bars, liquids, shampoos, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure, see U.S. Pat. 4, 835,148, Barford et al., issued May 30, 1989; incorporated herein by reference in its entirety.

The surfactant component of the compositions useful in the subject invention are selected from anionic, nonionic, zwitterionic, amphoteric and ampholytic surfactants, as well as mixtures of these surfactants. Such surfactants are well known to those skilled in the detergency art.

The cleaning compositions useful in the subject invention can optionally contain, at their art-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers*, North American Edition (1986), published by Allured Publishing Corporation, which is incorporated herein by reference in its entirety.

Combination Actives

A. Anti-Inflammatory Agents

An anti-inflammatory agent may be included as an active along with the active agents, for better activity. A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia cordifolia*), and Guggal (extracted from plants in the genus Commiphora, particularly *Commiphora mukul*), may be used.

B. Retinoids

In a preferred desquamatory composition useful in the subject invention, a retinoid, preferably retinoic acid, is included as an active along with the active agents. The inclusion of a retinoid increases the desquamation benefits of the composition. A safe and effective amount of a retinoid may be added to the compositions useful in the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

C. Antimicrobial Agents

In a preferred composition useful in the subject invention, an antimicrobial agent is included as an active along with the active agents. The inclusion of an antimicrobial agent increases the desquamation benefits of the composition. As used herein, "antimicrobial agent" means a compound capable of destroying microbes, preventing the development of microbes or preventing the pathogenic action of microbes.

A safe and effective amount of an antimicrobial agent may be added to compositions useful in the subject invention, preferably from about 0.001% to about 5%, more preferably from about 0.01% to about 2%, more preferably still from about 0.05% to about 1% of the compositions. Preferred antimicrobial agents useful in the subject invention are benzoyl peroxide, erythromycin, tetracycline, clindamycin, azelaic acid, and sulfur resorcinol.

D. Antiandrogens

In a preferred composition useful in the subject invention, an antiandrogen is included as an active along with the active agents. As used herein, "antiandrogen" means a compound capable of correcting androgen-related disorders by interfering with the action of androgens at their target organs. The target organ for the subject invention is mammalian skin.

E. Sunscreens and Sunblocks

Exposure to ultraviolet light can result in excessive scaling of the stratum corneum. Therefore, in a preferred composition useful in the subject invention, a sunscreen or sunblock is included as an active along with the actives of the subject invention.

A wide variety of conventional sunscreening agents are suitable for use in combination with the desquamation agents. Sagarin, et al., at Chapter VIII, pages 189 et seq., of *Cosmetics Science and Technology*, disclose numerous suitable agents, incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and dipropyleneglycol esters); Cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; [3-(4'- methylbenzylidene bornan-2-one) and 4-isopropyl-di-benzoylmethane.

Of these, 2-ethylhexyl-p-methoxycinnamate, 4,4'-t-butyl methoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethylamino-benzoate, 2-phenylbenzimidazole-5 -sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used as an added active in compositions useful in the subject invention. The sunscreening agent must be compatible with the desquamation agents. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

In a preferred composition of the subject invention, an anti-oxidant/radical scavenger is included as an active along with the active desquamation agents. Antioxidants/radical scavengers enhance the desquamation benefits of the subject invention by providing additional protection against UV radiation which can cause increased scaling in the stratum corneum.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

G. Chelators

In a preferred desquamatory composition useful in the subject invention, a chelating agent is included as an active along with the active agents. As used herein, "chelating agent" means an active agent capable of removing a metal ion from a system by forming a complex so that the metal ion cannot readily participate in or catalyze chemical reactions. The inclusion of a chelating agent increases the desquamation benefits of the composition by providing added protection against UV radiation which can contribute to excessive scaling.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furildioxime and derivatives thereof.

H. Anti-dandruff Actives

In a preferred composition of the subject invention formulated for application to the scalp, an anti-dandruff agent is included as an active along with the active desquamation agents. Anti-dandruff agents enhance the desquamation benefits of the subject invention by further preventing and treating the effects of flaking on the scalp. A particularly preferred anti-dandruff agent is zinc pyridinethione.

I. Glycolic Acid

In a preferred composition of the subject invention, glycolic acid is included as an active along with the subject desquamation agents. Preferably, the composition comprises from about 0.1% to about 10%, more preferably from about 0.2% to about 5%, also preferably from about 0.5% to about 2% glycolic acid.

Delivery Methods for the Topical Compositions

The topical compositions useful for the methods of the instant invention can be delivered from a variety of delivery devices. The following are two nonlimiting examples.

Medicated Cleansing Pads

The compositions useful herein can be incorporated into a medicated cleansing pad. Preferably these pads comprise from about 50% to about 75% by weight of one or more layers of nonwoven fabric material and from about 20% to about 50% by weight of a liquid composition deliverable from the nonwoven fabric material comprising hydroxy acid comprising salicylic acid and a subject zwitterionic surfactant, or mixture of such surfactants. These pads are described in detail in U.S. Pat. No. 4,891,228, to Thaman et al., issued Jan. 2, 1990; and U.S. Pat. No. 4,891,227, to Thaman et al., issued Jan. 2, 1990; both of which are incorporated by reference herein in their entirety.

Dispensing Devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The fluid comprises hydroxy acid comprising salicylic acid and a subject zwitterionic surfactant, or mixture of such surfactants.

The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matic, Mount Vernon, N.Y.

METHODS FOR DESQUAMATION AND TREATMENT OF ACNE

The subject invention relates to methods of removing scales from the stratum corneum of mammals. Such methods comprise topically applying to the skin or scalp an effective amount of the compositions of the subject invention. The term "effective amount", as used herein, means an amount sufficient to provide a scale removal benefit. The composition can be applied for several days, weeks, months or years at appropriate intervals: from about three times a day to about once every three days, preferably from about twice a day to once every other day, also preferably about once a day until satisfactory desquamation has been achieved.

The subject compositions may also be used for one or more of the following: reducing the appearance of large pores, reducing imperfections and/or blemishes in skin color, relieving dryness, eliminating dry rough spots, improving the skin's ability to retain moisture and/or protect itself from environmental stresses, reducing the appearance of fine lines and wrinkles, improving appearance and skin tone, increasing skin firmness and/or suppleness, increasing skin glow and clarity, and/or increasing the skin renewal process.

Typically, in each application, an effective coating of the skin or scalp is achieved by applying from about 0.004 mg/cm$^2$ to about 0.1 mg/cm$^2$ each of hydroxy acid comprising salicylic acid and a subject zwitterionic surfactant, or mixture of such surfactants, more preferably from about 0.02 mg/cm$^2$ to about 0.06 mg/cm$^2$, also preferably about 0.04 mg/cm$^2$.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example I

A topical composition is prepared by combining the following components utilizing conventional mixing techniques.

| Ingredient | % Weight |
| --- | --- |
| Water | 50.67 |
| Triethanolamine | 0.66 |
| Cetyl Betaine | 6.66 |
| Disodium EDTA | 0.01 |
| Ethanol (95%) | 40.00 |
| Salicylic Acid | 2.00 |

The above composition is applied to the face to remove scales at a dose enough to deposit 2 mg of the composition per cm$^2$ skin, once a day. As desquamation progresses, application is reduced to once very other day.

Example II

A cleaning composition is prepared by combining the following ingredients, using conventional mixing techniques:

| Ingredient | % Weight |
| --- | --- |
| Water | 44.75 |
| Tetrasodium EDTA | 0.12 |
| Cetyl Betaine | 3.33 |
| Sodium methyl cocoyl taurate | 41.67 |
| Cocoamidopropyl hydroxysultaine | 6.00 |
| Salicylic Acid | 2.00 |
| Cocoamidopropyl betaine | 1.43 |
| Hydroxypropyl methylcellulose | 0.50 |
| Glycolic Acid | 0.20 |
| Perfume | 0.12 |

The cleaning composition is applied to the face twice a day to treat acne. An amount enough to deposit 3 mg of the composition per $cm^2$ skin is used. As existant acne subsides, frequency is reduced to once a day.

Example III

The following hair tonic is prepared by mixing the ingredients according to conventional mixing techniques:

| Ingredient | % Weight |
| --- | --- |
| Triethanolamine lauryl sulfate | 17.0 |
| Coconut diethanol amide | 2.0 |
| Hydroxypropyl methyl cellulose[1] | 0.2 |
| Corn syrup (80% solids)[2] | 30.0 |
| Dimethylpolysiloxane | 1.0 |
| Cationic cellulose[3] | 0.5 |
| Ethyl alcohol (SDA 40) | 9.0 |
| Vinyl carboxy polymer[4] | 0.7 |
| Salicylic acid | 1.5 |
| Cocoamidopropyl Betaine | 3.5 |
| Perfume, color, preservative | 1.0 |
| Water | 33.6 |

Acid or base to pH 6.5
[1]Methocel E4M (Dow Chemical)
[2]42 Dextrose equivalent (Staley 1300)
[3]Polymer JR 400
[4]Carbopol 941 (BF Goodrich)

The composition is applied to the scalp every other day to treat dandruff. A dose of 5 mg of the composition per $cm^2$ skin is applied and then washed off.

Example IV

The following topical gel is prepared by mixing the ingredients according to conventional mixing techniques:

| Ingredients | % Weight |
| --- | --- |
| Alcohol SD-40 (95%) | 40.00 |
| Salicylic Acid | 2.00 |
| Disodium EDTA | 0.005 |
| Cetyl Betaine | 6.66 |
| Water | 47.335 |

The gel is applied to the face at a dose of 0.2 mg composition per $cm^2$ skin three times a day to remove scales. As desquamation progresses, application may be reduced to once a day.

Example V

The following lotion is prepared by mixing the ingredients according to conventional mixing techniques:

| Ingredient | % Weight |
| --- | --- |
| Water | q.s |
| Glycerin | 10.0 |
| Petrolatum | 2.5 |
| Cetyl Alcohol | 1.8 |
| Cyclomethicone and Dimethicone Copolyol | 1.5 |
| Stearyl Alcohol | 1.2 |
| Isopropyl Palmitate | 1.0 |
| Dimethicone | 0.5 |
| Sodium Hydroxide | 0.34 |
| Lanolin Acid | 0.25 |
| Polyethyleneglycol-100 Stearate | 0.25 |
| Stearic Acid | 0.25 |
| Methylparaben | 0.2 |
| Titanium Dioxide | 0.15 |
| EDTA | 0.1 |
| Salicylic Acid | 4.0 |
| Cocoamidopropyl Betaine | 5.0 |

The above lotion is applied to the hands once a day at a dose of 0.75 mg composition per $cm^2$ skin. As desquamation progresses, frequency of application may be reduced to once every two days.

Example VI

The following emulsion is prepared by mixing the following ingredients according to conventional mixing techniques:

| Ingredient | % Weight |
| --- | --- |
| Water | q.s. |
| PPG-14 Butyl Ether | 8.0 |
| Cetyl Betaine | 2.0 |
| Glycerin | 4.0 |
| Salicylic Acid | 2.0 |
| Stearyl Alcohol | 1.5 |
| Salcare SC 95 | 1.5 |
| Cetyl Alcohol | 1.5 |
| Dimethicone | 1.0 |
| Silica (DC Antifoam) | 0.5 |
| Steareth-21 | 0.45 |
| Steareth-2 | 0.05 |
| Tetrasodium EDTA | 0.02 |

The above lotion is applied to the face once a day at a dose of 0.60 mg composition per $cm^2$ skin. As desquamation progresses, frequency of application may be reduced to once every two days.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A topical composition for desquamation in mammalian skin comprising:

a) desquamation actives consisting essentially of:

(i) a safe and effective amount of zwitterionic surfactant having the structure:

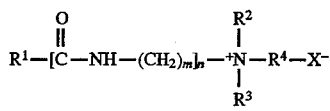

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkylene, unsubstituted or mono-substituted with hydroxy, having from 1 to about 5 carbon atoms; and X is selected from the group consisting of $CO_2$, $SO_3$ and $SO_4$; and (ii) a safe and effective amount of salicylic acid; and b) a topical carrier; the composition being in the form of a topical product.

2. The composition of claim 1 wherein:
(a) the concentration of salicylic acid is from about 0.1% to about 10%; and
(b) the concentration of zwitterionic surfactant is from about 0.1% to about 10%.

3. The composition of claim 2 wherein:
(a) $R^2$ and $R^3$ are selected from the group consisting of $CH_3$, $CH_2CH_2OH$ and $CH_2CH_2CH_2OH$;
(b) X is $CO_2$ or $SO_3$; and
(c) m is 2 or 3.

4. The composition of claim 3 wherein $R^4$ has from 1 to about 3 carbon atoms when X is $CO_2$, and $R^4$ has from about 2 to about 4 carbon atoms when X is $SO_3$.

5. The composition of claim 4 wherein:
a) $R^1$ has from about 11 to about 18 carbon atoms;
b) $R^2$ and $R^3$ are $CH_3$; and
c) $R^4$ has 1 carbon atom when X is $CO_2$; and $R^4$ has 3 carbon atoms when X is $SO_3$.

6. The composition of claim 5 wherein:
(a) $R^4$ has 1 carbon atom;
(b) X is $CO_2$;
(c) m is 3; and
(d) n is 1.

7. The composition of claim 5 wherein:
(a) $R^4$ has 3 carbon atoms;
(b) X is $SO_3$;
(c) m is 3; and
(d) n is 1.

8. The composition of claim 5 wherein:
(a) the concentration of salicylic acid is from about 0.2% to about 5%; and
(b) the concentration of zwitterionic surfactant is from about 0.2% to about 5%.

9. The composition of claim 2 wherein the composition further comprises from about 0.2% to about 5% of glycolic acid.

10. The composition of claim 4 wherein the zwitterionic surfactant is behenyl betaine.

11. The composition of claim 5 wherein the zwitterionic surfactant is cocoamidopropyl betaine or cetyl propyl hydroxy sultaine.

12. The composition of claim 5 wherein the zwitterionic surfactant is cetyl betaine.

13. The composition of claim 1 wherein said topical product is selected from the group consisting of lotions, creams, gels, sticks, sprays, ointments, pastes, mousses, cosmetics, and cleansers.

14. The composition of claim 1, further comprising an active selected from the group consisting of retinoids, antimicrobials, antiandrogens, sunscreens, sunblocks, antioxidants/radical scavengers, chelators, anti-dandruff agents, glycolic acid, and combinations thereof.

15. A topical composition suitable for desquamation in mammalian skin comprising:
(a) a safe and effective amount of zwitterionic surfactant having the structure:

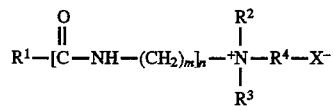

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkylene, unsubstituted or mono-substituted with hydroxy, having from 1 to about 5 carbon atoms; and X is selected from the group consisting of $CO_2$, $SO_3$ and $SO_4$;

(b) a safe and effective amount of salicylic acid;
(c) a nonionic, anionic or cationic emulsifier and/or surfactant, and
(d) a topical carrier;
the composition being in the form of a topical product.

16. The composition of claim 15 wherein:
(a) the concentration of salicylic acid is from about 0.1% to about 10%; and
(b) the concentration of zwitterionic surfactant is from about 0.1% to about 10%.

17. The composition of claim 15 wherein:
(a) $R^2$ and $R^3$ are selected from the group consisting of $CH_3$, $CH_2CH_2OH$ and $CH_2CH_2CH_2OH$;
(b) X is $CO_2$ or $SO_3$; and
(c) m is 2 or 3.

18. The composition of claim 17 wherein $R^4$ has from 1 to about 3 carbon atoms when X is $CO_2$, and $R^4$ has from about 2 to about 4 carbon atoms when X is $SO_3$.

19. The composition of claim 18 wherein:
a) $R^1$ has from about 11 to about 18 carbon atoms;
b) $R^2$ and $R^3$ are $CH_3$; and
c) $R^4$ has 1 carbon atom when X is $CO_2$; and $R^4$ has 3 carbon atoms when X is $SO_3$.

20. The composition of claim 18 wherein:
(a) the concentration of salicylic acid is from about 0.2% to about 5%; and
(b) the concentration of zwitterionic surfactant is from about 0.2% to about 5%.

21. The composition of claim 18 wherein the zwitterionic surfactant is selected from the group consisting of behenyl betaine, cocoamidopropyl betaine, cetyl propyl hydroxy sultaine, cetyl betaine and combinations thereof.

22. The composition of claim 21 wherein the zwitterionic surfactant is cocoamidopropyl betaine.

23. The composition of claim 21 wherein the zwitterionic surfactant is cetyl betaine.

24. The composition of claim 15 wherein the composition comprises a nonionic, anionic or cationic emulsifier.

25. The composition of claim 15 wherein the composition comprises a nonionic, anionic or cationic surfactant.

26. The composition of claim 15, further comprising an active selected from the group consisting of retinoids, antimicrobials, antiandrogens, sunscreens, sunblocks, antioxidants/radical scavengers, chelators, anti-dandruff agents, glycolic acid, and combinations thereof.

27. The composition of claim 26 wherein the composition further comprises from about 0.2% to about 5% of glycolic acid.

28. A method of treating acne in mammalian skin comprising topically applying to a mammal susceptible to or suffering from acne a safe and effective amount of a composition comprising:
  a) anti-acne actives consisting essentially of:
    (i) a safe and effective amount of salicylic acid; and
    (ii) a safe and effective amount of zwitterionic surfactant having the structure:

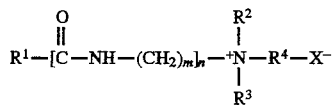

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkylene, unsubstituted or mono-substituted with hydroxy, having from 1 to about 5 carbon atoms; and X is selected from the group consisting of $CO_2$, $SO_3$ and $SO_4$; and
  b) a topical carrier.

29. The method of claim 28 wherein:
  (a) $R^2$ and $R^3$ are selected from the group consisting of $CH_3$, $CH_2CH_2OH$ and $CH_2CH_2CH_2OH$;
  (b) X is $CO_2$ or $SO_3$; and
  (c) m is 2 or 3.

30. The method of claim 29 wherein:
  (a) the amount of salicylic acid applied is from about 0.004 mg/cm$^2$ skin to about 0.1 mg/cm$^2$ skin; and
  (b) the amount of zwitterionic surfactant applied is from about 0.004 mg/cm$^2$ skin to about 0.1 mg/cm$^2$ skin.

* * * * *